United States Patent [19]
Ando et al.

[11] Patent Number: 5,407,600
[45] Date of Patent: Apr. 18, 1995

[54] STABLE AQUEOUS ALUMINA SOL AND METHOD FOR PREPARING THE SAME

[75] Inventors: Mikio Ando; Isao Yogo; Takanobu Kikawa, all of Sodegaura, Japan

[73] Assignee: Nissan Chemical Industries, Ltd., Tokyo, Japan

[21] Appl. No.: 915,612

[22] Filed: Jul. 21, 1992

[30] Foreign Application Priority Data

Jul. 23, 1991 [JP] Japan .................................. 3-182617
Jul. 24, 1991 [JP] Japan .................................. 3-184716

[51] Int. Cl.$^6$ ............................................. B01J 13/00
[52] U.S. Cl. ................................. 252/313.1; 423/115; 423/118.1; 423/124
[58] Field of Search .................... 252/313.1; 423/115, 423/118.1, 124

[56] References Cited

U.S. PATENT DOCUMENTS

| | | | |
|---|---|---|---|
| 2,798,049 | 7/1957 | White et al. | 252/313.1 |
| 2,915,475 | 12/1959 | Bugosh | 252/313.1 |
| 2,992,262 | 7/1961 | Sears et al. | 556/183 |
| 3,020,242 | 2/1962 | McCarthney et al. | 252/313.1 |
| 3,031,417 | 4/1962 | Bruce | 252/313.1 |
| 3,031,418 | 4/1962 | Bugosh | 252/313.1 |
| 3,207,578 | 9/1965 | Brown et al. | 252/313.1 |

FOREIGN PATENT DOCUMENTS 32-3367  5/1954  Japan .
60-166220  8/1985  Japan .

*Primary Examiner*—Robert L. Stoll
*Assistant Examiner*—Daniel S. Metzmaier
*Attorney, Agent, or Firm*—Oliff & Berridge

[57] ABSTRACT

A stable aqueous sol of amorphous alumina containing $Al_2O_3$ up to 15% by weight and 0.1 to 0.5 gram equivalent of an anion of acid to 1 mol of aluminum in the sol, in which the colloidal particles of amorphous alumina have a controlled thickness in a range of 20 to 100 millimicrons and a uniform length in a range of 200 to 500 millimicrons is produced by a process comprising feeding an aqueous solution of an acid into an aqueous slurry containing 1 to 7% by weight of metallic aluminum, 10 to 200 ppm by weight as $SiO_2$ of a water-soluble silicate and 0 to 20 ppm by weight of a water-soluble sulfate as $SO_4$ to the water in the slurry while maintaining the slurry at a temperature of 80° C. to boiling point under normal pressure, said acid being in an amount of 0.1 to 0.5 gram equivalent to 1 mol of the metallic aluminum in said slurry, at a rate of 0.001 to 0.03 gram equivalent of the acid to 1,000 g of the water in the slurry per minute, and continuing heating the slurry after completion of the feeding of the acid at a temperature of 80° C. to boiling point of the slurry until a sol of amorphous alumina having a uniform length of 200 to 500 millimicrons is formed.

30 Claims, No Drawings

STABLE AQUEOUS ALUMINA SOL AND METHOD FOR PREPARING THE SAME

BACKGROUND OF THE INVENTION

1. Field of the Invention

The present invention relates to an improvement in aqueous alumina sol, particularly to a stable aqueous sol of amorphous alumina having a uniform length of 200 to 500 millimicrons and a controlled thickness of 20 to 100 millimicrons, and the method for preparing the sols.

2. Description of Prior Art

Japanese patent publication No. Sho 32-3367 (1957) discloses a method for preparing an aqueous sol of alumina by a process comprising reacting metallic aluminum directly with water in the presence of an acid such as inorganic or organic.

Japanese patent laid-open publication No. Sho 60-166220 (1985) discloses methods for preparing aqueous sols of amorphous alumina in fibrous form by a process comprising adding metallic aluminum into an aqueous solution of organic acid and heating the solution at a high temperature to obtain a reaction mixture, and followed by further adding an organic acid and metallic aluminum into the reaction mixture. However, the sols obtained by the method can not give sufficient properties to products obtained by using the sols, for example, carriers for catalysts, etc.

SUMMARY OF THE INVENTION

It is an object of the present invention to provide an improved sol of amorphous alumina.

It is another object of the present invention to provide a method for preparing efficiently such a stable aqueous sol of amorphous alumina as having improved properties.

The sol of the present invention is a stable aqueous sol of amorphous alumina containing $Al_2O_3$ up to 15% by weight and 0.1 to 0.5 gram equivalent of an anion of acid to 1 mol of aluminum in the sol, in which the colloidal particles of amorphous alumina have a thickness in a range of 20 to 100 millimicrons and a uniform length in a range of 200 to 500 millimicrons.

The method for preparing the sol of the present invention comprises feeding an aqueous solution of an acid into an aqueous slurry containing 1 to 7% by weight of metallic aluminum, 10 to 200 ppm by weight as $SiO_2$ of a water-soluble silicate and 0 to 20 ppm by weight of a water-soluble sulfate as $SO_4$ to the water in the slurry while maintaining the slurry at a temperature of 80° C. to boiling point under normal pressure, said acid being in an amount of 0.1 to 0.5 gram equivalent to 1 mol of the metallic aluminum in said slurry, at a rate of 0.001 to 0.03 gram equivalent of the acid to 1,000 g of the water in the slurry per minute, and continuing heating the slurry after completion of the feeding of the acid at a temperature of 80° C. to boiling point of the slurry under normal pressure until a sol of amorphous alumina having a uniform length of 200 to 500 millimicrons is formed.

DETAILED DESCRIPTION OF THE INVENTION

The aqueous slurry of metallic aluminum may be prepared by dispersing in water a metallic aluminum in such an amount as resulting a concentration of 1 to 7%, preferably, 2 to 6% by weight of aluminum in the slurry. It is preferred to use a metallic aluminum in powdery form, and having a purity of 99.6% or higher and a particle size in weight average of 10 to 100 microns. Desired water for use in the slurry is one having a high purity such as, for example, a deionized water or a distilled water.

As the acid to be added into the slurry, there may be used inorganic or organic acid such as, for example, hydrochloride, formic acid or acetic acid, though hydrochloride is most preferable. The acid is preferably fed into the slurry in a form of an aqueous solution having a concentration of usually 10 to 20%, preferably, 12 to 17% by weight of the acid. It is preferable to add the acid in an amount of 0.1 to 0.5 gram equivalent to 1 mol of the metallic aluminum in the slurry. The aqueous solution of the acid is fed continuously or intermittently into the slurry maintained at a temperature of 80° C. to boiling point under normal pressure at a rate of 0.001 to 0.03 gram equivalent to 1,000 g of the water in the slurry per minute.

Silicate ions are made to be present in the slurry in an amount over 10 ppm, preferably, 10 to 200 ppm by weight as $SiO_2$ to the water in the slurry at any stage before or after the addition of the acid, so long as the presence of the silicate ions in the slurry is attained before particles of amorphous alumina having a particle size of less than 3 millimicrons formed in the slurry begins to grow in the slurry. However, it is preferable to introduce the silicate ions before addition of the acid into the slurry in such a method as, for example, adding a water-soluble silicate or silicic acid to the slurry of the metallic aluminum or to the water for preparing the slurry.

The silicate ions in the slurry may be monomeric or polymeric, though monomeric ions are preferable. The monomeric silicate ions may be introduced into the slurry as an aqueous solution of a water-soluble silicate such as, for example, orthosilicate, sesquisilicate, metasilicate, etc., of sodium, potassium, lithium, ammonium, quaternary ammonium or amine. The silicate ions may be introduced into the slurry in a form of an aqueous solution of silicic acid or polysilicic acid having a particle size less than about 3 millimicrons which is prepared by contacting an aqueous solution of a water-soluble alkali metal silicate, for example, sodium water glass with a cation exchange material such as a cation exchange resin in the hydrogen form.

Sulfate ions may be made present together with the silicate ions in the slurry to control the distribution of the thickness of the colloidal particles of amorphous alumina formed in the slurry. Suitable amount of the sulfate ions is over 5 ppm preferably, 5 to 20 ppm by weight as $SO_4$ to the water in the slurry. The sulfate ions are also introduced into the slurry at any stage before or after the addition of the acid, so long as the presence of the sulfate ions in the slurry is attained before particles of amorphous alumina having a size of less than 3 millimicrons formed in the slurry begins to grow to colloidal particles of amorphous alumina. However, it is preferable to introduce the sulfate ions before addition of the acid into the slurry in such a method as, for example, adding a water-soluble sulfate to the slurry of the metallic aluminum or the water for preparing the slurry. Sulfate ions are introduced into the slurry as an aqueous solution of a water soluble sulfate such as for example, sodium, potassium, lithium or ammonium sulfate.

Heating of the slurry under agitation is still continued at 80° C. to boiling point of the slurry under normal pressure after the completion of the addition of the acid until a sol of amorphous alumina having a uniform length of 200 to 500 millimicrons is formed. The heating is usually completed in about 10 to 20 hours.

The remaining metallic aluminum and other insoluble materials in the sol after completion of the heating may be removed from the sol by conventional method such as, for example, filtration, centrifugal separator, etc., thereby to obtain a purified sol of amorphous alumina. The sol so obtained may be concentrated up to a range of less than about 15% by weight as $Al_2O_3$ by conventional method such as, for example, evaporation, reverse osmosis, etc. It is preferable to give a concentration of about 1 to 12% by weight of $Al_2O_3$ to the sol for stable products.

The colloidal particles of amorphous alumina in the sol produced by the method of the present invention may be observed in a photograph taken through electronic microscope. When the particles are formed in the presence of silicate ions and in the absence of sulfate ions in the slurry, the particles have a uniform thickness in a range of 40 to 100 millimicrons and a uniform length in a range of 200 to 500 millimicrons. The length is about 5 to 10 times the thickness. A single particle in the photograph appears to be formed as a result of aggregation parallel in each other of fibrous particles which are less thick than the colloidal particles. When the colloidal particles are formed in the presence of both the silicate ions and the sulfate ions in the slurry, the particles have also a uniform length in a range of 200 to 500 millimicrons, while the thickness of the particles are not uniform and are distributed variously in a range of 20 to 100 millimicrons. The particles less thick appear to be resulted from the aggregation of less number of the fibrous particles.

Colloidal particles of amorphous alumina formed in the absence of the silicate ions or formed in the presence of the silicate ions in an amount less than 10 ppm by weight as $SiO_2$ to the water in the slurry have a length less than 200 millimicrons. The length of the colloidal particles of amorphous alumina formed in the slurry increase with increase in the amount over 10 ppm by weight as $SiO_2$ of the silicate ions to the water in the slurry, while the thickness of the particles formed in the slurry does not vary with the increase in the amount of the silicate ions. The silicate ions in an amount more than 100 ppm by weight as $SiO_2$ in the slurry do not serve as increasing any more the length of the colloidal particles.

It is believed that particles of amorphous alumina having a particle size of less than 3 millimicrons formed in the slurry grow in length and thickness of the particles, and the silicate ions existing in the slurry promote the growing more in length than in thickness so that fine fibrous particles are formed in the slurry and serve as aggregating the fine fibrous particles parallel in each other to form the colloidal particles of the present invention, while the sulfate ions existing with the silicate ions in the slurry serve as preventing the fine fibrous particles from aggregation so as to form colloidal particles of various thickness.

It is not preferable to use in the slurry a metallic aluminum having a poor purity, since it often causes impure ions and insoluble materials in the slurry and in the sol produced. A metallic aluminum having a purity higher than 99.6% is satisfactory. It is preferable to use a metallic aluminum having a particle size in weight average of 10 to 100 microns for preparing at first the slurry to control the process efficiently though the size of the metallic aluminum in the slurry is gradually reduced with proceeding of the reaction of the aluminum with the acid in the slurry.

Too high a content of the metallic aluminum in the slurry as exceeding 7% by weight is not preferable, since a large amount of metallic aluminum remains in the sol at the end point of the process, or otherwise a large amount of the acid to be added is necessary to reduce the amount of metallic aluminum remaining in the sol which has a high concentration of $Al_2O_3$ that would cause the sol unstable. When the content of the metallic aluminum in the slurry is below 1% by weight, the sol produced has a low concentration of $Al_2O_3$ and it is necessary to remove a large amount of water from the sol to concentrate it. Additional supplying of the metallic aluminum into the slurry may be carried out with exhausting of aluminum by proceeding of the reaction of aluminum when the slurry contains a low content of aluminum, though it makes the process somewhat complicated and inefficient.

It is not preferable to add into the slurry too much amount of the acid as exceeding 0.5 gram equivalent to 1 mol of aluminum in the slurry, since the length of the colloidal particles of amorphous alumina in the sol produced tend to be shorter than 200 millimicrons. On the contrary, when the amount of the acid to be added into the slurry is less than 0.1 gram equivalent to 1 mol of aluminum in the slurry, the reaction of the aluminum with the acid in the slurry tends to be slow. It is also not preferable to feed the acid in such a low speed as 0.001 gram equivalent or less to 1,000 g of the water in the slurry per minute, since the process is not efficient. Too high a speed of the feeding of the acid as exceeding 0.03 gram equivalent to 1,000 g of the water in the slurry per minute should be avoided, since the length of the colloidal particles of amorphous alumina in the sol produced tend to be shorter than 200 millimicrons.

It is preferable to maintain the slurry throughout the process at a temperature of 80° C. to boiling point of the slurry under normal pressure in order to promote the reaction of the aluminum with the acid and the growing of the particles in the slurry.

The aqueous sol of amorphous alumina according to the present invention has an excellent stability and a relatively low viscosity. The sol may be used in various fields such as, for example, paper making, surface-treating agent for fibers or cloths, binder for refractories and carriers for catalysts, etc. Liquid compositions comprising the sol show improvement in thixotropic property, binding effect and film formability. Dried products from compositions comprising the sol show also improvement in water-retaining property, in preventing the products from electric charging, flexibility, etc.

EXAMPLE 1

700 g of a deionized water, 30 ppm by weight as $SiO_2$ of sodium metasilicate to the water and 15.4 g of a metallic aluminum having a particle size in weight average of 60 microns and a purity of 99.8% by weight were charged into a glass reactor to obtain a slurry of the metallic aluminum. The slurry was heated up to a temperature of 98° C. Into the slurry maintained at the temperature was fed 21 g of an aqueous solution (A) having a concentration of 13% by weight of hydrochloride under agitation in five minutes. Heating under agitation of the slurry after completion of the addition of the acid was further continued for 20 minutes at 98° C.

Then, 40 g of aqueous solution (A) of hydrochloride was again fed into the slurry maintained at 98° C. under agitation in 90 minutes. Heating under agitation of the slurry after completion of the addition of the acid was further continued for 12 hours at 98° C. Then the product was filtered. There was obtained 600 g of an aqueous sol having a concentration of 3.8% by weight of $Al_2O_3$. The sol was concentrated by evaporation under a reduced pressure up to a concentration of 10.5% by weight of $Al_2O_3$. There was obtained 217 g of an aqueous sol.

The concentrated sol had a pH of 3.92 and a viscosity of 700 cp at 20° C. The colloidal particles in the sol had a uniform thickness of 50 millimicrons and a uniform length of about 300 millimicrons-according to observation by electronic microscope. The colloidal particles in the photograph by electronic microscope appeared as one resulted from aggregation of fine particles in fibrous form. X-ray diffraction chart of the particles showed amorphous form.

EXAMPLE 2

In this example, experiments No. 1 to 6 were carried out in the same manner as in example 1 except that the amounts of the silicate ions were varied as shown in table 1.

The colloidal particles in these sols obtained were observed likewise in example 1. The thickness of the colloidal particles in experiments No. 1 to 6 were almost the same as that in example 1, while the length of the colloidal particles increased with increase in the amount of the silicate ions in the slurry as shown in table 1.

TABLE 1

| experiment No. | silicate ions as $SiO_2$ (ppm) | length of particles (m$\mu$) |
|---|---|---|
| 1 | 0 | 100 to 150 |
| 2 | 10 | 200 to 400 |
| 3 | 50 | 250 to 500 |
| 4 | 100 | 300 to 500 |
| 5 | 200 | 300 to 500 |
| 6 | 300 | 300 to 500 |

EXAMPLE 3

700 g of a deionized water, 30 ppm by weight as $SiO_2$ of sodium metasilicate to the water and 38.4 g of the same metallic aluminum as used in example 1 were charged into a glass reactor to obtain a slurry of the metallic aluminum. The slurry was heated up to a temperature of 98° C. Into the slurry maintained at the temperature was fed 21 g of an aqueous solution (A) having a concentration of 13% by weight of hydrochloride under agitation in five minutes. Heating under agitation of the slurry after completion of the addition of the acid was further continued for 20 minutes at 98° C.

Then, 160 g of aqueous solution (A) of hydrochloride was again fed into the slurry maintained at 98° C. under agitation in 90 minutes. Heating under agitation of the slurry after completion of the addition of the acid was further continued for 17 hours at 98° C. Then the product was filtered. There was obtained 680 g of an aqueous sol having a concentration of 10.2% by weight of $Al_2O_3$.

The sol had a pH of 3.92 and a viscosity of 800 cp at 20° C. The colloidal particles in the sol had a uniform thickness of 50 millimicrons and a uniform length of about 300 millimicrons according to observation by electronic microscope. The colloidal particles in the photograph by electronic microscope appeared as one resulted from aggregation of fine particles in fibrous form. X-ray diffraction chart of the particles showed amorphous form.

Comparative Example 1

In this example, 61 g of aqueous solution (A) of hydrochloride was fed in 5 minutes while the other were carried out in the same manner as in example 1. The colloidal particles of the sol produced had a thickness of 40 to 100 millimicrons and a length of 100 to 150 millimicrons which was 2 to 3 times the thickness.

Comparative Example 2

In this example, sodium sulfate in amount of 30 ppm by weight as $SO_4$ was added instead of sodium metasilicate in example 1 while the other were carried out in the same manner as in example 1. The colloidal particles of the sol produced had the same thickness and length as those of the sol in comparative example 1, and the length was 2 to 3 times the thickness.

EXAMPLE 4

This example was carried out in the same manner as in example 1 except that a slurry was prepared by further adding to the water sodium sulfate in amount of 20 ppm by weight as $SO_4$ to the water. The produced sol before concentration contained 3.5% by weight of $Al_2O_3$. The concentrated sol contained 10.3% by weight of $Al_2O_3$, and had a pH of 4.02 and a viscosity of 1480 cp at 20° C. The colloidal particles in a photograph by electronic microscope had a uniform length of about 300 millimicrons, while the thickness of these particles distributed in a range of 20 millimicrons at minimum to 100 millimicrons at maximum. The X-ray diffraction chart of the particles showed an amorphous pattern.

EXAMPLE 5

In this example, experiments No. 7 to 11 were carried out in the same manner as in example 4 except that the amounts as $SiO_2$ of the silicate were varied as shown in table 2.

All of the colloidal particles of the sols produced had almost the same thickness as those of the sol in example 4, while the length increased with increase in the amount of $SiO_2$ as shown in table 2.

TABLE 2

| experiment No. | silicate ions as $SiO_2$ (ppm) | length of particles (m$\mu$) |
|---|---|---|
| 7 | 0 | 100 to 150 |
| 8 | 10 | 200 to 400 |
| 9 | 50 | 250 to 500 |
| 10 | 100 | 300 to 500 |
| 11 | 200 | 300 to 500 |

EXAMPLE 6

In this example, experiments No. 12 to 15 were carried out in the same manner as in example 4 except that the amount as $SO_4$ of the sulfate was varied as 5 ppm in No. 12, 10 ppm in No. 13, 20 ppm in No. 14 and 50 ppm in No. 15.

All of the colloidal particles of the sols produced had a length of about 300 millimicrons, while the thickness distributed likewise in example 4, and the rate of number of the particles having a thickness of 20 millimicrons at minimum to the total increased with increase in the amount from 5 to 20 ppm of $SO_4$, though the rate in 50 ppm of $SO_4$ was almost the same as that in 20 ppm of $SO_4$.

EXAMPLE 7

This example was carried out in the same manner as that in example 3 except that a slurry was prepared by further adding sodium sulfate in amount of 20 ppm by weight as $SO_4$ to the water in the slurry.

The sol produced contained 10.1% by weight of $Al_2O_3$, and had a pH of 3.96 and a viscosity of 1950 cp at 20° C.

The colloidal particles of the sol had a uniform length of about 300 millimicrons, and the thickness of these particles distributed from 20 millimicrons at minimum to 100 millimicrons at maximum. The X-ray diffraction chart of the particles showed amorphous pattern.

Comparative Example 3

A sol was obtained in the same manner as in example 4 except that 61 g of aqueous solution (A) of hydrochloride was fed into the slurry in 5 minutes. The colloidal particles in the sol had a length of 100 to 150 millimicrons and a thickness of 40 to 100 millimicrons, and the length was 2 to 3 times the thickness.

What is claimed is:

1. A method for preparing a stable aqueous sol of amorphous alumina containing $Al_2O_3$ in an amount up to 15% by weight and an anion of acid in an amount of 0.1 to 0.5 gram equivalent to 1 mol of aluminum in the sol, in which the colloidal particles of amorphous alumina have a uniform thickness in a range of 40 to 100 millimicrons and a uniform length in a range of 200 to 500 millimicrons, the length being 5 to 10 times the thickness, comprising feeding an acid into an aqueous slurry of metallic aluminum while maintaining the slurry at a temperature of 80° C. to boiling point under normal pressure, said slurry containing 1 to 7% by weight of the metallic aluminum and said acid being in an amount of 0.1 to 0.5 gram equivalent to 1 mol of the metallic aluminum in said slurry, at a rate of 0.001 to 0.03 gram equivalent of the acid to 1,000 g of the water in the slurry per minute, adding into the slurry a water-soluble silicate or silicic acid in an amount of 10 to 200 ppm by weight as $SiO_2$ to the water in the slurry before particles of amorphous alumina having a particle size of less than 3 millimicrons formed in the slurry begins to grow in the slurry, and continuing heating the slurry after completion of the feeding of the acid at a temperature of 80° C. to boiling point of the slurry under normal pressure until a sol of amorphous alumina having a uniform length of 200 to 500 millimicrons is formed.

2. A method for preparing a stable aqueous sol of amorphous alumina as claimed in claim 1, wherein the metallic aluminum in the slurry has at first a particle size in weight average of 10 to 100 microns and a purity of 99.6% by weight or more.

3. A method for preparing a stable aqueous sol of amorphous alumina as claimed in claim 1, wherein the acid to be fed into the slurry is an aqueous solution having a concentration of 10 to 20% by weight of hydrochloride, formic acid or acetic acid.

4. A method for preparing a stable aqueous sol of amorphous alumina as claimed in claim 1, wherein the acid to be fed into the slurry is an aqueous solution having a concentration of 12 to 17% by weight of hydrochloride.

5. A method for preparing a stable aqueous sol of amorphous alumina as claimed in claim 1, wherein the water-soluble silicate is a silicate of sodium, potasium, lithium, ammonium, or an amine.

6. A method for preparing a stable aqueous sol of amorphous alumina as claimed in claim 5, wherein the water-soluble silicate of an amine is a silicate of a quaternary ammonium.

7. A method for preparing a stable aqueous sol of amorphous alumina as claimed in claim 1, wherein the silicic acid is an aqueous solution of silicic acid not containing silica having a size larger than 3 millimicrons.

8. A method for preparing a stable aqueous sol of amorphous alumina as claimed in claim 1, wherein the silicic acid is an acidic aqueous solution of silicic acid which is obtained by contacting an aqueous solution of sodium water glass with a cation-exchange resin in the hydrogen form.

9. A method for preparing a stable aqueous sol of amorphous alumina, further comprising in addition to the method in claim 1 a step where insoluble materials remaining in the sol obtained by the method in claim 4 are removed from the sol, and thereafter a step of concentrating the sol up to a range of less than 15% by weight of $Al_2O_3$.

10. A method for preparing a stable aqueous sol of amorphous alumina containing $Al_2O_3$ in an amount up to 15% by weight and an anion of acid in an amount of 0.1 to 0.5 gram equivalent to 1 mol of aluminum in the sol, in which the colloidal particles of amorphous alumina have a uniform thickness in a range of 40 to 100 millimicrons and a uniform length in a range of 200 to 500 millimicrons, the length being 5 to 10 times the thickness, comprising feeding an aqueous solution having a concentration of 10 to 20% by weight of hydrochloride into an aqueous slurry containing 1 to 7% by weight of metallic aluminum having a particle size in weight average of 10 to 100 microns and a water-soluble silicate in an amount of 10 to 200 ppm by weight as $SiO_2$ to the water in the slurry while maintaining the slurry at a temperature of 80° C. to boiling point under normal pressure, said acid being in an amount of 0.1 to 0.5 gram equivalent to 1 mol of the metallic aluminum in said slurry, at a rate of 0.001 to 0.03 gram equivalent of the acid to 1,000 g of the water in the slurry per minute, and continuing heating the slurry after completion of the feeding of hydrochloride at a temperature of 80° C. to boiling point of the slurry under normal pressure until a sol of amorphous alumina having a uniform length of 200 to 500 millimicrons is formed.

11. A method for preparing a stable aqueous sol of amorphous alumina as claimed in claim 10, wherein the metallic aluminum in the slurry has a purity of 99.6% by weight or more.

12. A method for preparing a stable aqueous sol of amorphous alumina as claimed in claim 10, wherein the water-soluble silicate is a silicate of sodium, potasium, lithium, ammonium, or an amine.

13. A method for preparing a stable aqueous sol of amorphous alumina as claimed in claim 12, wherein the water-soluble silicate of an amine is a silicate of a quaternary ammonium.

14. A method for preparing a stable aqueous sol of amorphous alumina, further comprising in addition to the method in claim 10 a step where insoluble materials remaining in the sol obtained by the method in claim 10 are removed from the sol, and thereafter a step of concentrating the sol up to a range of less than 15% by weight of $Al_2O_3$.

15. A method for preparing a stable aqueous sol of amorphous alumina containing $Al_2O_3$ in an amount up to 15% by weight and an anion of acid in an amount of 0.1 to 0.5 gram equivalent to 1 mol of aluminum in the sol, in which the colloidal particles of amorphous alumina have a thickness distributed in a range of 20 to 100 millimicrons and a uniform length in a range of 200 to 500 millimicrons, comprising feeding an acid into an aqueous slurry of metallic aluminum while maintaining the slurry at a temperature of 80° C. to boiling point under normal pressure, said slurry containing 1 to 7% by weight of a metallic aluminum and said acid being in an amount of 0.1 to 0.5 gram equivalent to 1 mol of the metallic aluminum in said slurry, at a rate of 0.001 to 0.03 gram equivalent of the acid to 1,000 g of the water in the slurry per minute, adding into the slurry a water-soluble silicate or silicic acid in an amount of 10 to 200 ppm by weight as $SiO_2$ to the water in the slurry and a water-soluble sulfate in an amount of 5 to 20 ppm by weight as $SO_4$ to the water in the slurry before particles of amorphous alumina having a particle size of less than 3 millimicrons formed in the slurry begins to grow in the slurry, and continuing heating the slurry after completion of the feeding of the acid at a temperature of 80° C. to boiling point of the slurry under normal pressure until a sol of amorphous alumina having a uniform length of 200 to 500 millimicrons are formed.

16. A method for preparing a stable aqueous sol of amorphous alumina as claimed in claim 15, wherein the metallic aluminum in the slurry has at first a particle size in weight average of 10 to 100 microns and a purity of 99.6% by weight or more.

17. A method for preparing a stable aqueous sol of amorphous alumina as claimed in claim 15, wherein the acid to be fed into the slurry is an aqueous solution having a concentration of 10 to 20% by weight of hydrochloride, formic acid or acetic acid.

18. A method for preparing a stable aqueous sol of amorphous alumina as claimed in claim 15, wherein the acid to be fed into the slurry is an aqueous solution having a concentration of 12 to 17% by weight of hydrochloride.

19. A method for preparing a stable aqueous sol of amorphous alumina as claimed in claim 15, wherein the water-soluble silicate is a silicate of sodium, potassium, lithium, ammonium, or an amine.

20. A method for preparing a stable aqueous sol of amorphous alumina as claimed in claim 19, wherein the water-soluble silicate of an amine is a silicate of a quaternary ammonium.

21. A method for preparing a stable aqueous sol of amorphous alumina as claimed in claim 15, wherein the silicic acid is an aqueous solution of silicic acid not containing silica having a size larger than 3 millimicrons.

22. A method for preparing a stable aqueous sol of amorphous alumina as claimed in claim 15, wherein the silicic acid is an acidic aqueous solution of silicic acid which is obtained by contacting an aqueous solution of sodium water glass with a cation-exchange resin in the hydrogen form.

23. A method for preparing a stable aqueous sol of amorphous alumina as claimed in claim 15, wherein the water-soluble sulfate is an aqueous solution of sodium, potassium, lithium or ammonium sulfate.

24. A method for preparing a stable aqueous sol of amorphous alumina, further comprising in addition to the method in claim 15 a step where insoluble materials remaining in the sol obtained by the method in claim 19 are removed from the sol, and thereafter a step of concentrating the sol up to a range of less than 15% by weight of $Al_2O_3$.

25. A method for preparing a stable aqueous sol of amorphous alumina containing $Al_2O_3$ in an amount up to 15% by weight and an anion of acid in an amount of 0.1 to 0.5 gram equivalent to 1 mol of aluminum in the sol, in which the colloidal particles of amorphous alumina have a thickness distributed in a range of 20 to 100 millimicrons and a uniform length in a range of 200 to 500 millimicrons, comprising feeding an aqueous solution having a concentration of 10 to 20% by weight of hydrochloride into an aqueous slurry containing 1 to 7% by weight of metallic aluminum having a particle size in weight average of 10 to 100 microns, a water-soluble silicate in an amount of 10 to 200 ppm by weight as $SiO_2$ to the water in the slurry and a water-soluble sulfate in an amount of 5 to 20 ppm by weight as $SO_4$ to the water in the slurry while maintaining the slurry at a temperature of 80° C. to boiling point under normal pressure, said acid being in an amount of 0.1 to 0.5 gram equivalent to 1 mol of the metallic aluminum in said slurry, at a rate of 0.001 to 0.03 gram equivalent of the acid to 1,000 g of the water in the slurry per minute, and continuing heating the slurry after completion of the feeding of hydrochloride at a temperature of 80° C. to boiling point of the slurry under normal pressure until a sol of amorphous alumina having a uniform length of 200 to 500 millimicrons is formed.

26. A method for preparing a stable aqueous sol of amorphous alumina as claimed in claim 25 wherein the metallic aluminum in the slurry has a purity of 99.6% by weight or more.

27. A method for preparing a stable aqueous sol of amorphous alumina as claimed in claim 25, wherein the water-soluble silicate is a silicate of sodium, potassium, lithium, ammonium, or an amine.

28. A method for preparing a stable aqueous sol of amorphous alumina as claimed in claim 27, wherein the water-soluble silicate of an amine is a silicate of a quaternary ammonium.

29. A method for preparing a stable aqueous sol of amorphous alumina as claimed in claim 25, wherein, the sulfate is sodium, potassium, lithium or ammonium sulfate.

30. A method for preparing a stable aqueous sol of amorphous alumina, further comprising in addition to the method in claim 25 a step where insoluble materials remaining in the sol obtained by the method in claim 25 are removed from the sol, and thereafter a step of concentrating the sol up to a range of less than 15% by weight of $Al_2O_3$.

* * * * *

UNITED STATES PATENT AND TRADEMARK OFFICE
CERTIFICATE OF CORRECTION

PATENT NO. : 5,407,600
DATED : April 18, 1995
INVENTOR(S) : Mikio ANDO, Isao YOGO, and Takanobu KIKAWA It is certified that error appears in the above-indentified patent and that said Letters Patent is hereby corrected as shown below:

Column 2, line 8, change "hydrochloride," to --hydrogen chloride,--; and
lines 8 and 9, change "hydrochloride" to --hydrogen chloride,--.

Column 4, lines 65-66, change "hydrochloride" to --hydrogen chloride--.

Column 5, line 1, change "hydrochloride" to --hydrogen chloride--;
lines 52-53, change "hydrochloride" to --hydrogen chloride--; and
line 56, change "hydrochloride" to --hydrogen chloride--.

Column 6, lines 7-8, change "hydrochloride" to --hydrogen chloride--.

Column 7, lines 21-22, change "hydrochloride" to --hydrogen chloride--.

Signed and Sealed this

Seventh Day of May, 1996

Attest:

BRUCE LEHMAN

Attesting Officer                Commissioner of Patents and Trademarks